(12) United States Patent
Kitaoka et al.

(10) Patent No.: US 7,532,313 B2
(45) Date of Patent: May 12, 2009

(54) FLUORESCENCE DETECTOR AND LIQUID CHROMATOGRAPH HAVING THE FLUORESCENCE DETECTOR

(75) Inventors: Mitsuo Kitaoka, Kyoto (JP); Ryutaro Oda, Kyoto (JP); Masahide Gunji, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 12/062,480

(22) Filed: Apr. 3, 2008

(65) Prior Publication Data

US 2008/0246954 A1    Oct. 9, 2008

(30) Foreign Application Priority Data

Apr. 5, 2007    (JP) .............................. 2007-098982

(51) Int. Cl.
*G01N 21/00* (2006.01)
(52) U.S. Cl. ............................................ 356/72; 422/7
(58) Field of Classification Search ................... 356/72; 422/70, 7
See application file for complete search history.

(56) References Cited

U.S. PATENT DOCUMENTS

2007/0116600 A1 * 5/2007 Kochar et al. .................. 422/65
2007/0243600 A1 * 10/2007 Lair et al. ................. 435/287.2

FOREIGN PATENT DOCUMENTS

JP    2000-346805 A    12/2000

* cited by examiner

*Primary Examiner*—Kara E Geisel
*Assistant Examiner*—Abdullahi Nur
(74) *Attorney, Agent, or Firm*—Cheng Law Group PLLC

(57) ABSTRACT

The fluorescence detector includes: a flow cell provided on a flow passage for flowing a sample; a sample temperature control block for keeping the flow cell and the flow passage located on the sample inlet side of the flow cell at a constant temperature; an excitation optical system; a fluorescence optical system having a photodetector and used for guiding fluorescence emitted from a sample flowing through the flow cell to the photodetector and detecting the fluorescence; a photodetector temperature control block for keeping the photodetector at a constant temperature; and a temperature control unit having a simultaneous temperature control block united with both the temperature control blocks and a temperature control system provided to be in contact with the simultaneous temperature control block to heat and/or cool the simultaneous temperature control block.

8 Claims, 2 Drawing Sheets

FLUORESCENCE DETECTOR AND LIQUID CHROMATOGRAPH HAVING THE FLUORESCENCE DETECTOR

BACKGROUND OF THE INVENTION

1. Field of the Invention

The present invention relates to a fluorescence detector to be used as a detector in, for example, a liquid chromatograph, and more particularly, a fluorescence detector having a temperature control device for controlling the temperature of a sample to be introduced into a flow cell, and a liquid chromatograph having such a fluorescence detector.

2. Description of the Related Art

A liquid chromatograph has a detector for detecting each of the components of a sample separated by an analysis column, and an example of such a detector includes a fluorescence detector. In a fluorescence detector, a sample to be analyzed is introduced into a transparent container called 'flow cell', the flow cell is irradiated with light having a specific wavelength as excitation light, and the amount of fluorescence emitted from the excited sample is measured by a photodetector to determine the concentration or amount of each of the components of the sample.

However, many samples to be analyzed by a liquid chromatograph show a strong dependence on temperature of the amount of emitted fluorescence, and therefore in a case when fluorescence emitted from such a sample is detected under conditions where the temperature of the sample varies, there has been a problem that the amount of fluorescence detected by a photodetector varies with changes in the temperature of the sample, thereby making it impossible to obtain a good detection result.

In order to solve such a problem, a fluorescence detector having a heat exchanging portion provided upstream of a flow cell on a flow passage for flowing a sample and a temperature control system constituted from a Peltier device provided in the vicinity of the heat exchanging portion has been proposed (see, for example, Japanese Patent Application Laid-open No. 2000-346805), and this proposal has been carried out. This fluorescence detector is designed to allow heat exchange to be carried out between a sample passing through the heat exchanging portion and the temperature control system to control the temperature of the sample to be introduced into the flow cell by cooling.

Meanwhile, the sensitivity of a photodetector provided for detecting fluorescence emitted from a sample is also dependent on temperature. However, an error resulting from the temperature dependence of sensitivity of the photodetector is less than that resulting from the temperature dependence of the amount of fluorescence emitted from a sample, and therefore, conventionally, a higher priority has been given to keeping a sample to be introduced into a flow cell at a constant temperature.

However, some photoelectron multipliers as representative examples of photodetectors show a high rate of change of sensitivity with a temperature of 0.5%/° C. or higher. When such a photodetector whose sensitivity is strongly dependent on temperature is used, there is a case where the amount of fluorescence measured has a large error. Therefore, it has been necessary to select a photodetector whose sensitivity was weakly dependent on temperature to achieve higher sensitivity and highly-reproducible analytical results not dependent on its ambient temperature. However, this limited the choice of usable photodetectors, thereby causing an increase in the production cost of a detector.

Further, in a case where a photoelectron multiplier was used as a photodetector, there has been also a problem that the amount of dark current flowing through a multiplier tube was increased as the temperature of a detector was increased, thereby increasing noise.

SUMMARY OF THE INVENTION

It is therefore an object of the present invention to provide a fluorescence detector which can achieve higher reproducibility of detection results without increasing its production cost.

The present invention is directed to a fluorescence detector including: a flow cell provided on a flow passage for flowing a sample; a sample temperature control block for keeping the flow cell and the flow passage located on the sample inlet side of the flow cell at a constant temperature; an excitation optical system for guiding excitation light to the flow cell; a fluorescence optical system having a photodetector and used for guiding fluorescence emitted from a sample flowing through the flow cell to the photodetector for detecting the fluorescence; a photodetector temperature control block for keeping the photodetector at a constant temperature; and a temperature control unit having a simultaneous temperature control block united with both the temperature control blocks and a temperature control system provided to be in contact with the simultaneous temperature control block to heat and/or cool the simultaneous temperature control block.

The simultaneous temperature control block and the photodetector temperature control block may be formed into a single block, or the simultaneous temperature control block and the sample temperature control block may be formed into a single block. Alternatively, the simultaneous temperature control block, the photodetector temperature control block and the sample temperature control block may be formed into a single block. By doing so, it is possible to improve thermal conductivity between the temperature control blocks, thereby further enhancing the effect of temperature control.

Examples of the temperature control system include a Peltier device, and a temperature control system utilizing a cooling cycle while having a flow passage for circulating a cooling medium on which a compressor, a condenser, and a cooling part are provided.

Further, the present invention is also directed to a liquid chromatograph including: an analysis flow passage for sending a mobile phase; a sample injection portion for injecting a sample into the analysis flow passage; an analysis column provided downstream of the sample injection portion on the analysis flow passage to separate a sample injected from the sample injection portion into individual components; and a detector provided downstream of the analysis column on the analysis flow passage to detect each of the components separated by the analysis column, wherein the detector is a fluorescence detector according to the present invention.

Since the fluorescence detector according to the present invention includes the sample temperature control block for keeping the flow cell and the flow passage located on the sample inlet side of the flow cell at a constant temperature, the photodetector temperature control block for keeping the photodetector at a constant temperature, and the temperature control unit having the simultaneous temperature control block united with both the temperature control blocks and a temperature control system provided to be in contact with the simultaneous temperature control block to heat and/or cool the simultaneous temperature control block, by utilizing the existing temperature control system for controlling the temperature of the flow cell and the temperature of a sample to be introduced into the flow cell, it is also possible to control the temperature of the photodetector without providing another temperature control system. Therefore, according to the present invention, it is possible to provide a fluorescence detector less likely to be affected by ambient temperature. Further, since the fluorescence detector according to the present invention uses the existing temperature control system for controlling the temperature of the flow cell and the temperature of a sample to be introduced into the flow cell, it is possible to suppress an increase in its production cost.

Further, since the liquid chromatograph according to the present invention uses a fluorescence detector according to the present invention as the detector for detecting each of the components of a sample separated by the analysis column, it is possible to prevent the detection result of the photodetector from being affected by ambient temperature, thereby improving the reproducibility of analytical results.

DETAILED DESCRIPTION OF THE INVENTION

Figure 1A:
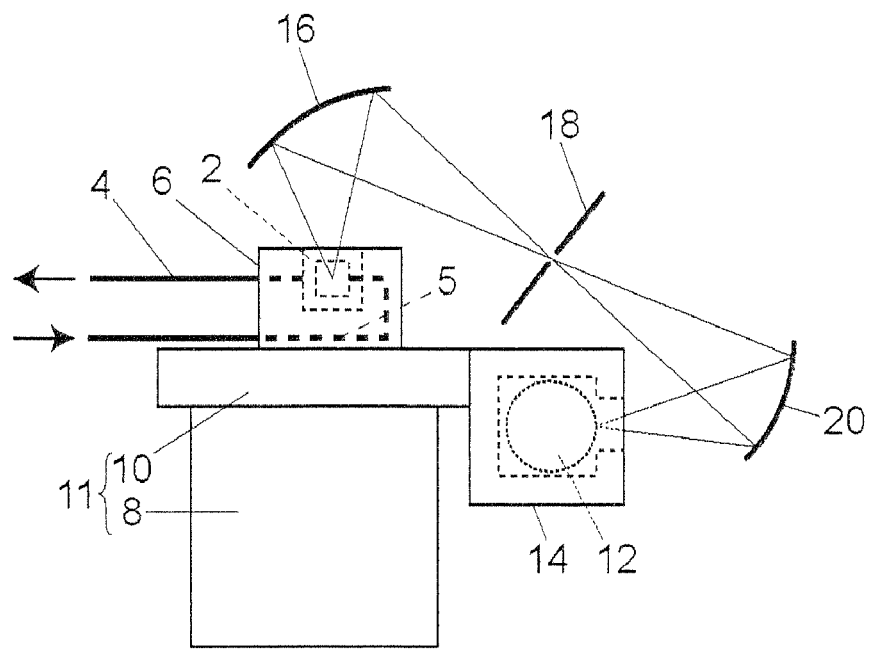
FIG. 1A is a front view of a fluorescence detector according to one embodiment of the present invention.
Figure 1B:
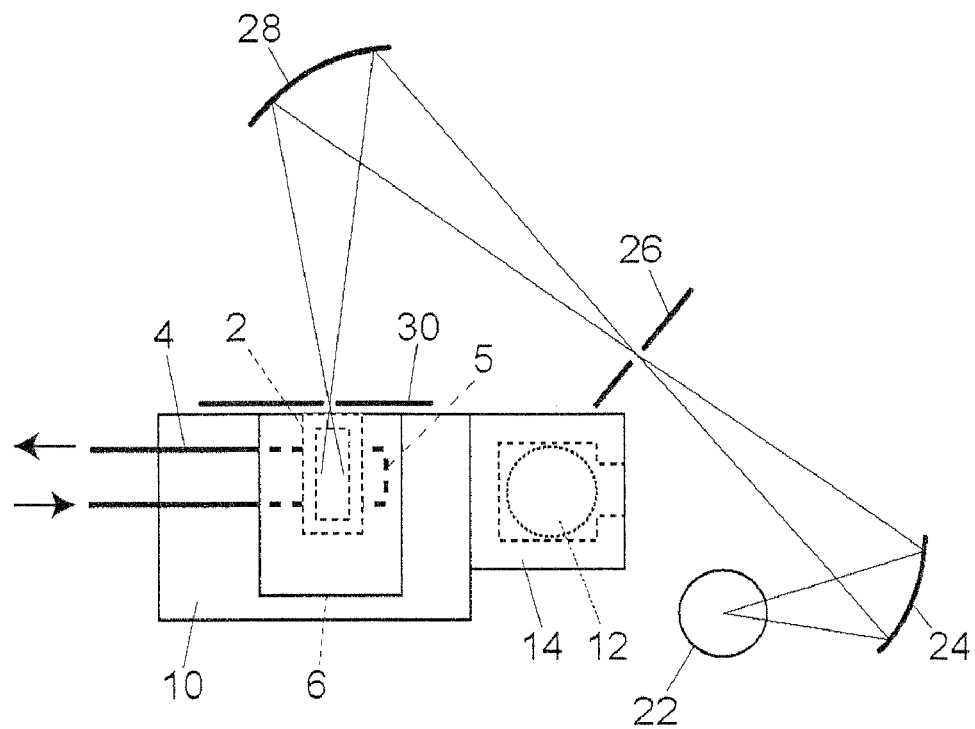
FIG. 1B is a plan view of the fluorescence detector shown in FIG. 1A.

A fluorescence detector according to one embodiment of the present invention will be described with reference to the accompanying drawings. FIG. 1A is a front view schematically showing the structure of the fluorescence detector according to one embodiment of the present invention, and FIG. 1B is a schematic plan view of the fluorescence detector.

A flow cell 2 constituted from a transparent container is provided on an analysis flow passage 4 for sending a sample. A space containing the flow cell 2 is accommodated in a sample temperature control block 6. On the analysis flow passage 4 located on the sample inlet side of the flow cell 2, a heat exchanging portion 5 for keeping a sample to be introduced into the flow cell 2 at a constant temperature is provided. The heat exchanging portion 5 is also accommodated in the sample temperature control block 6. The sample temperature control block 6 is formed of a heat conductive material such as aluminum.

In order to irradiate the flow cell 2 with excitation light, an excitation optical system for guiding excitation light to the flow cell 2 is provided. The excitation optical system has a xenon lamp as a light source 22, a condensing mirror 24, an inlet slit 26, a concave diffraction grating 28, and an outlet slit 30.

A photodetector 12 for detecting fluorescence emitted from a sample is provided in the vicinity of a temperature control unit 11. The photodetector 12 is, for example, a photoelectron multiplier. Further, a condensing mirror 16 for condensing fluorescence emitted from a sample, a slit 18 for allowing light condensed by the condensing mirror 16 to pass through, and a concave diffraction grating 20 for guiding light passed through the slit 18 to a detecting surface of the photodetector 12 are provided. The photodetector 12, the condensing mirror 16, the slit 18, and the diffraction grating 20 constitute a fluorescence optical system. It is to be noted that in FIG. 1A, the excitation optical system is not shown to facilitate understanding of the structure of the fluorescence optical system, and in FIG. 1B, the fluorescence optical system is not shown to facilitate understanding of the structure of the excitation optical system.

A photodetector temperature control block 14 is provided around the photodetector 12 to keep the photodetector 12 at a constant temperature. The photodetector temperature control block 14 is formed by a heat conductive material such as aluminum. The photodetector temperature control block 14 has an opening located on the detecting surface side of the photodetector 12 so that light guided by the diffraction grating 20 to the detecting surface of the photodetector 12 is not blocked.

The temperature control unit 11 is provided under the flow cell 2. The temperature control unit 11 has a heat conductive simultaneous temperature control block 10 and a temperature control system 8. The temperature control system 8 is in contact with the simultaneous temperature control block 10 and is constituted from a Peltier device for cooling and/or heating the simultaneous temperature control block 10 to keep the simultaneous temperature control block 10 at a constant temperature. The simultaneous temperature control block 10 is formed by a heat conductive material such as aluminum. The heat exchanging portion 5 consists of a part of the analysis flow passage 4 located on the sample inlet side of the flow cell 2, and is in close contact with the simultaneous temperature control block 10.

Instead of the Peltier device, a temperature control system utilizing a cooling cycle of a cooling medium may be used as the temperature control system 8. The temperature control system has a flow passage for circulating a cooling medium, on which a compressor for compressing the cooling medium, a condenser for condensing the cooling medium compressed by the compressor and a cooling part for cooling its surroundings by gasifying the cooling medium are provided.

The simultaneous temperature control block 10 is united with the sample temperature control block 6 and the photodetector temperature control block 14. A direction in which excitation light, with which the flow cell 2 is irradiated, travels, and a direction in which fluorescence emitted from a sample in the flow cell 2 travels intersect at right angles, and therefore the side surface of the sample temperature control block 6 has a window for allowing the excitation light to enter, and the top surface of the sample temperature control block 6 has a window for allowing the fluorescence to exit. The sample temperature control block 6 is provided on the top surface of the simultaneous temperature control block 10. The photodetector temperature control block 14 is provided on the side surface of the simultaneous temperature control block 10. The excitation optical system for guiding excitation light to the flow cell 2 accommodated in the sample temperature control block 6 and the fluorescence optical system for guiding fluorescence emitted from a sample in the flow cell 2 to the photodetector 12 are provided in different directions from each other to prevent interaction therebetween.

Since the sample temperature control block 6 is united with the simultaneous temperature control block 10, the simultaneous temperature control block 10 cooled and/or heated by the Peltier device 8 cools and/or heats the sample temperature control block 6 so that the temperature of the sample temperature control block 6 is controlled to be constant. This also makes it possible to keep the flow cell 2, the heat exchanging portion 5, and their surrounding space accommodated in the sample temperature control block 6 at a constant temperature. Further, since the photodetector temperature control block 14 is also united with the simultaneous temperature control block 10, the simultaneous temperature control block 10 cooled and/or heated by the Peltier device 8 cools and/or heats the photodetector temperature control block 14 so that the temperature of the photodetector temperature control block 14 is controlled to be constant. This also makes it possible to keep the photodetector 12 accommodated in the photodetector temperature control block 14 at a constant temperature.

The sample temperature control block 6 and the simultaneous temperature control block 10 may be formed into a single block as long as there is not a particular problem in analysis or product assembly. By doing so, it is possible to improve thermal conductivity between the sample temperature control block 6 and the simultaneous temperature control block 10, thereby making it possible to control the temperature of the space containing the flow cell 2 with a higher degree of accuracy. Further, the photodetector temperature control block 14 and the simultaneous temperature control block 10 may be formed into a single block. By doing so, it is possible to improve thermal conductivity between the photodetector temperature control block 14 and the simultaneous temperature control block 10, thereby making it possible to control the temperature of the photodetector 12 with a higher degree of accuracy. Alternatively, the simultaneous temperature control block 10, the sample temperature control block 6 and the photodetector temperature control block 14 may be formed into a single block.

It is to be noted that each of the sample temperature control block 6 and the photodetector temperature control block 14 can be formed by, for example, surrounding an object whose temperature is to be controlled with a heat conductive metal, and the heat conductive metal may be further surrounded with a heat insulator. Alternatively, each of the sample temperature control block 6 and the photodetector temperature control block 14 can also be formed by, for example, partially surrounding an object whose temperature is to be controlled with a heat conductive metal, and surrounding the heat conductive metal and a part of the object not surrounded with the heat conductive metal with a heat insulator.

Hereinafter, the operation of the fluorescence detector according to the present embodiment will be described.

A sample flowing through the analysis flow passage 4 is introduced into the heat exchanging portion 5 so that the temperature of the sample is controlled to be constant, and is then introduced into the flow cell 2. Light emitted from the light source 22 is condensed by the condensing mirror 24, passed through the inlet slit 26, and then diffracted by the diffraction grating 28 so that light having a specific wavelength exits from the outlet slit 30 as excitation light, and then the sample in the flow cell 2 is irradiated with the excitation light. Fluorescence emitted from the sample is condensed by the condensing mirror 16, passed through the slit 18, diffracted by the diffraction grating 20 and then guided to a detecting surface of the photodetector 12 kept at a constant temperature by the photodetector temperature control block 14 to detect the amount of the fluorescence.

Since the temperature of a sample to be irradiated with excitation light is controlled to be constant and the flow cell 2 and its vicinity are also kept at a constant temperature by the sample temperature control block 6, the amount of fluorescence emitted from the sample is not affected by ambient temperature. Further, since the temperature of the photodetector 12 is also controlled to be constant by the photodetector temperature control block 14, the sensitivity of the photodetector 12 is not affected by ambient temperature, and is therefore kept constant without fluctuation when the photodetector 12 detects the amount of fluorescence emitted from the sample.

Since the fluorescence detector is designed to allow the photodetector 12 to be kept at a constant temperature by using the temperature control system 8 for controlling the temperature of the flow cell 2 and the temperature of a sample to be introduced into the flow cell 2, it is not necessary to provide another temperature control system and to select a photodetector whose sensitivity is weakly dependent on temperature. This makes it possible to reduce production cost and therefore to provide a fluorescence detector which is not expensive but can achieve improved reproducibility of analytical results.

Figure 2:
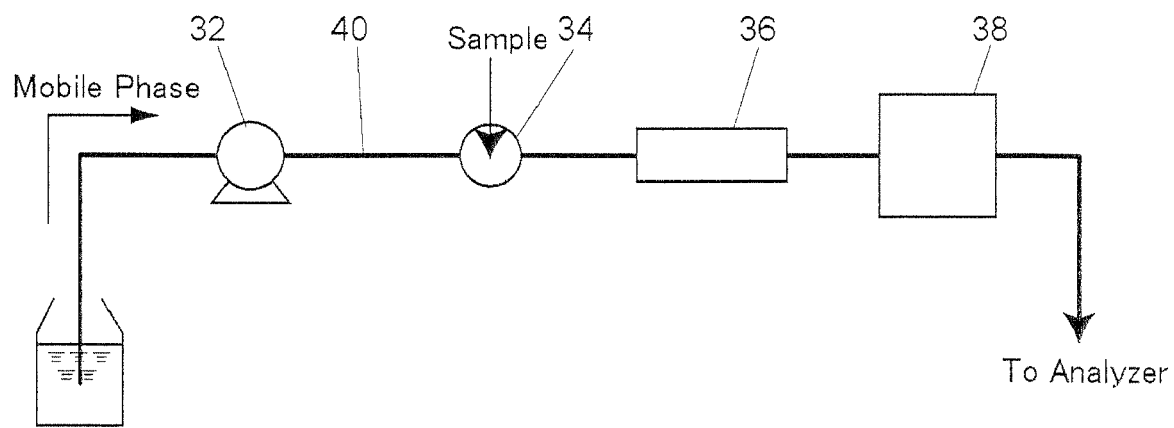
FIG. 2 is a schematic view showing the structure of a liquid chromatograph according to one embodiment of the present invention.

Next, a liquid chromatograph using the fluorescence detector according to the present invention will be described. FIG. 2 is a schematic diagram showing the structure of a liquid chromatograph according to one embodiment of the present invention. A mobile phase sent by a liquid sending pump 32 flows through an analysis flow passage 40 at a constant flow rate. The analysis flow passage 40 has a sample injection portion 34 for injecting a sample. Further, an analysis column 36 is provided downstream of the sample injection portion 34 to separate a sample injected from the sample injection portion 34 into individual components. Further, a detector 38 is provided downstream of the analysis column 36 to detect each of the components separated by the analysis column 36.

As the detector 38, the fluorescence detector according to the present invention, for example, the fluorescence detector according to one embodiment of the present invention shown in FIGS. 1A, 1B is used. The analysis flow passage 40 of the liquid chromatograph corresponds to the analysis flow passage 4 shown in FIGS. 1A, 1B, and an eluate containing a component of a sample separated by the analysis column 36 exchanges heat with the simultaneous temperature control block 10 so that the temperature of the eluate is controlled to be constant, and is then introduced into the flow cell 2.

As described above, since the liquid chromatograph according to the present invention uses a fluorescence detector according to the present invention as the detector 38, the detection results of the detector 38 are less likely to be affected by ambient temperature, thereby making it possible to perform analysis accurately.

What is claimed is:

1. A fluorescence detector comprising:
a flow cell provided on a flow passage for flowing a sample;
a sample temperature control block for keeping the flow cell and the flow passage located on the sample inlet side of the flow cell at a constant temperature;
an excitation optical system for guiding excitation light to the flow cell;
a fluorescence optical system having a photodetector and used for guiding fluorescence emitted from a sample flowing through the flow cell to the photodetector for detecting the fluorescence;
a photodetector temperature control block for keeping the photodetector at a constant temperature; and
a temperature control unit having a simultaneous temperature control block,
wherein the simultaneous temperature control block is (a) united with both the sample temperature control block and the photodetector temperature control block and (b) is in contact with a temperature control system which heats and/or cools the simultaneous temperature control block.

2. The fluorescence detector according to claim 1, wherein the simultaneous temperature control block and the photodetector temperature control block are formed into a single block.

3. The fluorescence detector according to claim 1, wherein the simultaneous temperature control block and the sample temperature control block are formed into a single block.

4. The fluorescence detector according to claim 1, wherein the simultaneous temperature control block, the photodetector temperature control block, and the sample temperature control block are formed into a single block.

5. The fluorescence detector according to claim 1, wherein the temperature control system is a Peltier device.

6. The fluorescence detector according to claim 1,
wherein the temperature control system has a flow passage for circulating a cooling medium, on which a compressor for compressing the cooling medium, a condenser provided downstream of the compressor to condense the cooling medium compressed by the compressor and a cooling part for cooling by gasifying the cooling medium are provided, and
wherein the cooling part is in contact with the simultaneous temperature control block.

7. The fluorescence detector according to claim 1,
wherein the sample temperature control block is provided on the top surface of the simultaneous temperature control block and the photodetector temperature control block is provided on the side surface of the simultaneous temperature control block, and
wherein a direction in which excitation light, with which the flow cell is irradiated, travels, and a direction in which fluorescence emitted from a sample in the flow cell travels intersect at right angles, and therefore the side surface of the sample temperature control block has a window for allowing the excitation light to enter and the top surface of the sample temperature control block has a window for allowing the fluorescence to exit, and
wherein the excitation optical system and the fluorescence optical system are provided in different directions from each other to prevent interaction therebetween.

8. A liquid chromatograph comprising:
an analysis flow passage for sending a mobile phase;
a sample injection portion for injecting a sample into the analysis flow passage;
an analysis column provided downstream of the sample injection portion on the analysis flow passage to separate a sample injected from the sample injection portion into individual components; and
a detector provided downstream of the analysis column on the analysis flow passage to detect each of the components separated by the analysis column, wherein the detector is the fluorescence detector according to claim 1.

* * * * *